United States Patent
Norton

(10) Patent No.: US 7,050,850 B2
(45) Date of Patent: May 23, 2006

(54) METHODS AND APPARATUS FOR REFORMING HIGH-VOLTAGE ELECTROLYTIC CAPACITORS

(75) Inventor: John D. Norton, New Brighton, MN (US)

(73) Assignee: Medtronic, Inc., Minneapolis, MN (US)

( * ) Notice: Subject to any disclaimer, the term of this patent is extended or adjusted under 35 U.S.C. 154(b) by 521 days.

(21) Appl. No.: 10/393,908

(22) Filed: Mar. 20, 2003

(65) Prior Publication Data
US 2004/0186519 A1 Sep. 23, 2004

(51) Int. Cl.
*A61N 1/39* (2006.01)

(52) U.S. Cl. .......................................................... 607/5
(58) Field of Classification Search ............... 607/4–30
See application file for complete search history.

(56) References Cited

U.S. PATENT DOCUMENTS

| 4,238,985 A | 12/1980 | Adachi |
| 4,830,006 A | 5/1989 | Haluska et al. |
| 4,971,058 A | 11/1990 | Pless et al. |
| 5,127,404 A | 7/1992 | Wyborny et al. |
| 5,265,588 A | 11/1993 | Nelson et al. |
| 5,312,441 A | 5/1994 | Mader et al. |
| 5,372,605 A | 12/1994 | Adams et al. |
| 5,439,482 A | 8/1995 | Adams et al. |
| 5,470,341 A | 11/1995 | Kuehn et al. |
| 5,690,685 A | 11/1997 | Kroll et al. |
| 5,792,188 A | 8/1998 | Starkweather et al. |
| 5,827,326 A | 10/1998 | Kroll et al. |
| 5,861,006 A | 1/1999 | Kroll |
| 5,861,106 A | 1/1999 | Olander |
| 5,899,923 A | 5/1999 | Kroll et al. |
| 5,926,362 A | 7/1999 | Muffoletto et al. |
| 6,006,133 A | 12/1999 | Lessar et al. |
| 6,032,075 A | 2/2000 | Pignato et al. |
| 6,096,062 A | 8/2000 | Silvian |
| 6,249,423 B1 | 6/2001 | O'Phelan et al. |
| 6,283,985 B1 | 9/2001 | Harguth et al. ................. 607/1 |

*Primary Examiner*—Scott M. Getzow
(74) *Attorney, Agent, or Firm*—Girma Wolde-Michael; Carol F. Barry

(57) ABSTRACT

A cardioverter/defibrillator of the type having at least one high voltage (HV) output capacitor having valve metal anode and cathode electrodes with an oxide formed over a majority of said anode and a wet electrolyte in fluid communication with the electrodes that is charged from a battery through a charging circuit including a HV step-up transformer and is adapted to be discharged through cardioversion/defibrillation (C/D) electrodes is disclosed. The HV output capacitor(s) periodically charge in a reform charge cycle to substantially a maximum or full charge at a reform charge rate slower than a C/D therapy charge rate, which also charges said HV output capacitor(s) to the maximum or full charge, to thereby reform deformed portions of the oxide.

33 Claims, 5 Drawing Sheets

Time required to charge capacitor at therapeutic rate (10 mA) after 11 autocap cycles as a function of autocap charge current.

Time required to charge capacitor at therapeutic rate (10 mA) after 11 autocap cycles as a function of autocap charge time.

METHODS AND APPARATUS FOR REFORMING HIGH-VOLTAGE ELECTROLYTIC CAPACITORS

RELATED APPLICATIONS

The following two non-provisional U.S. patent disclosures are hereby incorporated by reference herein; namely, U.S. patent application Ser. No. 10/261,066 entitled, "METHOD AND APPARATUS FOR MAINTAINING ENERGY STORAGE IN AN ELECTRICAL STORAGE DEVICE" and U.S. patent application Ser. No. 10/260,488 entitled, "APPARATUS AND METHOD FOR OPTIMIZING CAPACITOR CHARGE IN A MEDICAL DEVICE" both said disclosures on 30 Sep. 2002.

FIELD OF THE INVENTION

The present invention relates to the field high energy density capacitor oxide reformation for medical devices; in particular the present invention relates to implantable cardioverter-defibrillator (ICD) and automatic external defibrillator (AED) devices and provides improved methods and apparatus for reforming the oxides of electrodes of capacitors for such devices.

BACKGROUND OF THE INVENTION

The implementation and use of high voltage output systems within ICDs is well known. Generally, ICDs have high voltage (HV) output capacitors, typically valve metal electrolytic capacitors, which are typically charged to a substantially full (or maximum) preprogrammed charge via high current battery systems, such as silver vanadium oxide (SVO) battery cells, coupled to DC-to-DC voltage converters in order to generate cardioversion/defibrillation (C/D) shocks. An example of the high voltage charging system for an existing ICD is described in U.S. Pat. No. 5,372,605, for example. The HV output capacitors are charged up to the programmed voltage when tachyarrhythmia detection criteria are met and a C/D shock is to be delivered by discharging the HV output capacitors through the heart between C/D electrodes.

The term "valve metal" stands for a group of metals including aluminum, tantalum, niobium, titanium, zirconium, etc., all of which form adherent, electrically insulating, metal oxide dielectric films or layers upon anodic polarization in electrically conductive solutions. Wet electrolytic capacitors essentially consist of an anode electrode, a cathode electrode, a barrier or separator layer for separating the anode and cathode, and an electrolyte. In cylindrical electrolytic capacitors, the anode electrode is typically composed of wound anodized aluminum foil in which subsequent windings are separated by at least one separator layer. The anodes in a flat electrolytic capacitor (FEC) may consist of stacked sheets of aluminum that are electrically connected together. In another type of capacitor a valve metal powder is pressed, sintered and formed into a typically unitary anode electrode, and the anode is separated from at least one cathode by a electrically insulative separator layer as is known in the art and as described further below. For an FEC, typically a plurality of aluminum sheets are etched or perforated to increase surface area. For both FEC- and pressed and sintered-type capacitors, an oxide dielectric is formed upon on exposed surfaces of the anode (the pressed and sintered structure or etched or the perforated sheets) when the anode is immersed in a formation electrolyte while electrical current circulates therethrough during manufacture. Examples of electrolytic capacitors are disclosed, for example in commonly assigned U.S. Pat. No. 6,006,133 and in U.S. Pat. Nos. 6,249,423, 6,283,985, and 5,926,362.

In order to conserve ICD battery power, the HV output capacitors remain in an uncharged state when not in use. However, the metal oxide dielectric tends to degrade when the HV output capacitors are left in an uncharged state between charging to deliver C/D shocks. When it becomes necessary to charge the HV output capacitors, there can be a considerable leakage current occurring between the anode and cathode electrodes of the HV output capacitors. This leakage current can prolong the time that it takes to charge the HV output capacitors to the desired C/D voltage, and the delay can possibly delay necessary electrical therapy delivery to a patient. Moreover, this leakage current also requires that more battery energy be expended to charge the HV output capacitors to the desired C/D voltage. Consequently, the leakage current can further result in excessive consumption of limited battery power thereby decreasing the longevity of the ICD.

Thus, although such valve metal electrolytic capacitors have a relatively high energy density per volume, such capacitors tend to degrade electrochemically over time thereby increasing the charge time required to fully charge the HV output capacitor system. Similarly, the SVO battery cells also have a tendency to degrade electrochemically over time if they are not discharged due to the increased equivalent series resistance (ESR) within the battery that decreases the current output capabilities of the battery.

The conventional solution to both of these problems has been to conduct a periodic reforming of the high voltage output system of an ICD by rapidly charging the HV output capacitor system to its full rated voltage and then allowing discharge through a non-therapeutic load (e.g., discharge through a resistive load) or allowing discharge via leakage current(s). In this way, both the high current battery system and the HV output capacitor system are exercised so as to reform the electro-chemistries of each system, thereby reducing the impact on charge performance and component life due to electrochemical degradation over time. Originally, this reforming process was accomplished manually by having a patient visit the physician every two to three months, at that time the physician would fully charge the capacitor(s), but not deliver, a full voltage rated C/D therapy shock. Presently, the reforming of the high voltage output system is accomplished automatically by the ICD based on a fixed time period (e.g., every month, every six months), at the end of that a full charge cycle of the HV output capacitor system is automatically conducted. The physician can program the fixed time.

For example, for a typical HV output capacitor used in an ICD, the HV output capacitor will be charged during reforming maintenance to approximately 800 volts that requires the battery to provide approximately 55 joules of energy. This is a considerable expenditure of battery energy, which significantly reduces the longevity of the battery. Moreover, the prior art systems that periodically charge the HV output capacitors often end up charging the HV output capacitors when dielectric has not degraded to the point where the leakage current that would occur during the generation of a therapeutic waveform would present a problem. Consequently, while periodically reforming the HV output capacitor during periods of non-use to the HV output capacitor's peak voltage may reduce the leakage current during therapeutic waveform generation, the reduction in leakage current is accomplished at a significant cost in terms of battery and device longevity.

While this kind of simple periodic reform cycle was more than effective for early ICDs where the life span of the device was typically less than three years and the battery budget could easily support the periodic reform cycles, newer ICDs are smaller and have much longer life spans. An example of such an ICD that is used as a prophylactic device is described in U.S. Pat. No. 5,439,482. In these newer designs for an ICD, battery power is at more of a premium than in previous designs and the periodic reforming of the high voltage output system can represent a significant portion of the battery budget over the life of the device.

Alternate techniques for accomplishing reforming of the battery system and the HV output capacitor system are disclosed in U.S. Pat. Nos. 5,861,106, 5,899,923 and 5,690,685. In the '923 patent, a system is disclosed for measuring the leakage current of the HV output capacitor system at a relatively low voltage and using this value to estimate whether the HV output capacitor system needs to be reformed. By utilizing a low voltage test process, battery power is conserved and full voltage reforming is conducted only when it is determined that the HV output capacitor is in need of reforming. In the '685 patent, a technique is disclosed for measuring an electrical parameter of the battery system and using this value to determine whether the battery system needs to be reformed. Again, battery power is conserved by only performing a full voltage reform when it is determined that the internal resistance of the battery system has increased to the point where charge performance is degraded. A system for selectively reforming the high voltage output systems of an ICD based on the charge history and charge performance of the battery and capacitor systems so as to maintain charge performance while conserving battery power is disclosed in the above-referenced '106 patent.

While such approaches may offer promise, they suffer from the disadvantage of potentially requiring additional circuit within the ICD to implement. Therefore, it would be advantageous to develop a more efficient system and algorithm for reforming the oxide layers of the HV output capacitors and battery of an ICD. It would be advantageous to develop a simpler capacitor oxide layer reform system and algorithm or process that does not require significant additional circuitry within the ICD.

The rapid charging of the ICD capacitors to the full output voltage or a lesser reforming voltage to reform the oxide layers of the capacitor plates can result in very high local current densities that may result in localized oxide layer defects and residual stresses that can allow the capacitor to degrade further and be less efficient during subsequent shock therapy delivery or reform charge and discharge cycles. Moreover, the rapid charging of the HV output capacitors during the charge phase of the reform charge and discharge cycle increases resistive power losses within the battery, thereby decreasing device longevity. Therefore, it would also be advantageous to develop a capacitor oxide layer reform system and algorithm or process that reduces the extent of such oxide layer damage and resistive power losses.

BRIEF SUMMARY OF THE INVENTION

The inventor of the present invention discovered that slowing the rate of charging HV output capacitors to substantially maximum or full C/D therapy voltage when reforming the oxides of the capacitors substantially improves reformation of deformed oxide layers of the capacitor and results a more stable oxide which is not as susceptible of later deformation. That is, such relatively slower rate reformation charging of the capacitor to an essentially full charge provides an oxide that degrades to a lesser extent over time prior to a subsequent therapeutic charge-discharge C/D shock therapy delivery cycle or a subsequent non-therapeutic (i.e., reformation) cycle. Moreover, less rapid charging of the HV output capacitors during the charge phase of the reform charge cycle also appears to decrease resistive power losses within the battery, extending the life of the battery and the ICD or AED system.

Therefore, the present invention advantageously provides a capacitor oxide dielectric layer reform system, algorithm and process that reduces the rate of HV output capacitor charging for reformation charges relative to that of therapeutic charges to advantageously decrease subsequent oxide degradation (or deformation), thereby reducing future charging time and charging energy, and increasing the battery life of the ICD or AED.

A system and method of operating a cardioverter-defibrillator is provided in accordance with the present invention comprising detecting a malignant tachyarrhythmia of a heart, charging high voltage HV output capacitors to a C/D shock energy at a therapy charging rate, discharging the high voltage HV output capacitors through C/D electrodes of the cardioverter/defibrillator to deliver a C/D shock to a patient's heart, and as needed periodically charging the HV output capacitors to a maximum or full capacitor charge during reform at a reformation charging rate that is relatively slower than the C/D therapeutic charging rate to thereby create a more stable oxide dielectric on the anode of the high voltage HV output capacitors.

This summary of the invention has been presented here simply to point out some of the ways that the invention overcomes difficulties presented in the prior art and to distinguish the invention from the prior art and is not intended to operate in any manner as a limitation on the interpretation of claims that are presented initially in the patent application and that are ultimately granted.

BRIEF DESCRIPTION OF THE DRAWINGS

These and other advantages and features of the present invention will be more readily understood from the following detailed description of the preferred embodiments thereof, when considered in conjunction with the drawings, in that like reference numerals indicate identical structures throughout the several views, and wherein.

DETAILED DESCRIPTION OF THE PREFERRED EMBODIMENTS OF THE INVENTION

In the following detailed description, references are made to illustrative embodiments of methods and apparatus for carrying out the invention. It is understood that other embodiments can be utilized without departing from the scope of the invention. Preferred methods and apparatus are described for reforming ICD capacitors in a fashion that reduces subsequent degradation of the ICD capacitor oxide and minimizes the energy expenditure and drain on the ICD high voltage batteries.

Such ICD IPGs typically are formed having a housing that is hermetically sealed and, therefore, is impervious to body fluids, and a connector header for making electrical and mechanical connection with one or more leads bearing pacing, sensing and C/D electrodes adapted to be located in or around selected chambers of the heart. The housing is formed of a suitable, body-compatible material approved for medical use, such as titanium and is shaped physiologically so as to avoid sharp edges that might lead to tissue necrosis following implantation. Typically, the housing is formed having major opposed or parallel surfaces joined together by sides enclosing an interior housing chamber or cavity and having electrical feedthroughs extending therethrough and into the connector header. The housing cavity receives the battery(s) and the high voltage (HV) and low voltage (LV) electronic circuit that can comprise ICs, circuit boards and discrete components, e.g., but not limited to, the step-up transformer and the HV output capacitor(s). Although, there is no particular preferred embodiment of such an ICD, FIGS. 1 and 2 depict one form of such an ICD in that the present invention can be advantageously implemented.

Figure 1:
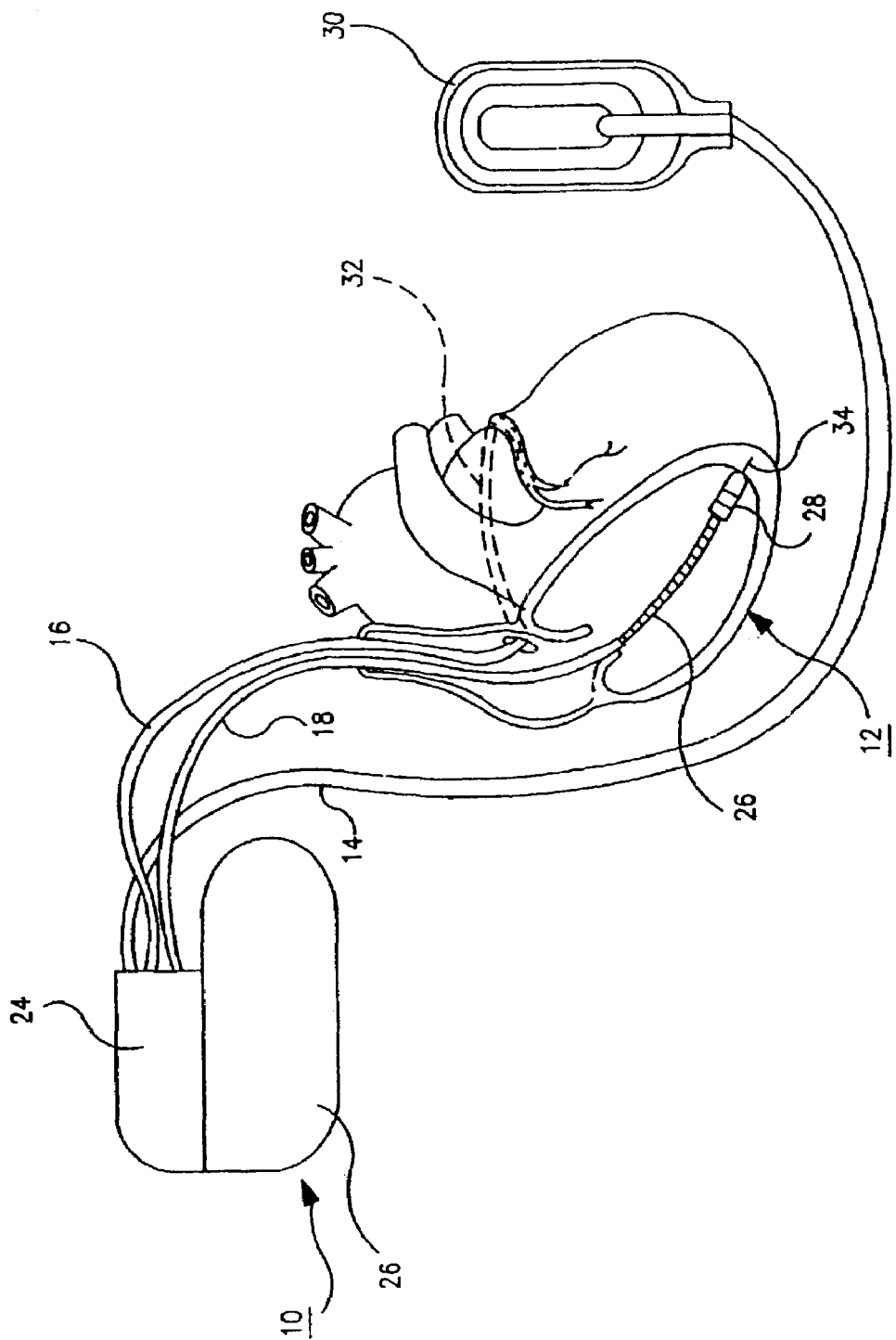
FIG. 1 illustrates the physical components of an ICD IPG and lead system extending to the heart illustrative of a type of ICD IPG in that the present invention may be advantageously practiced.
Figure 2:
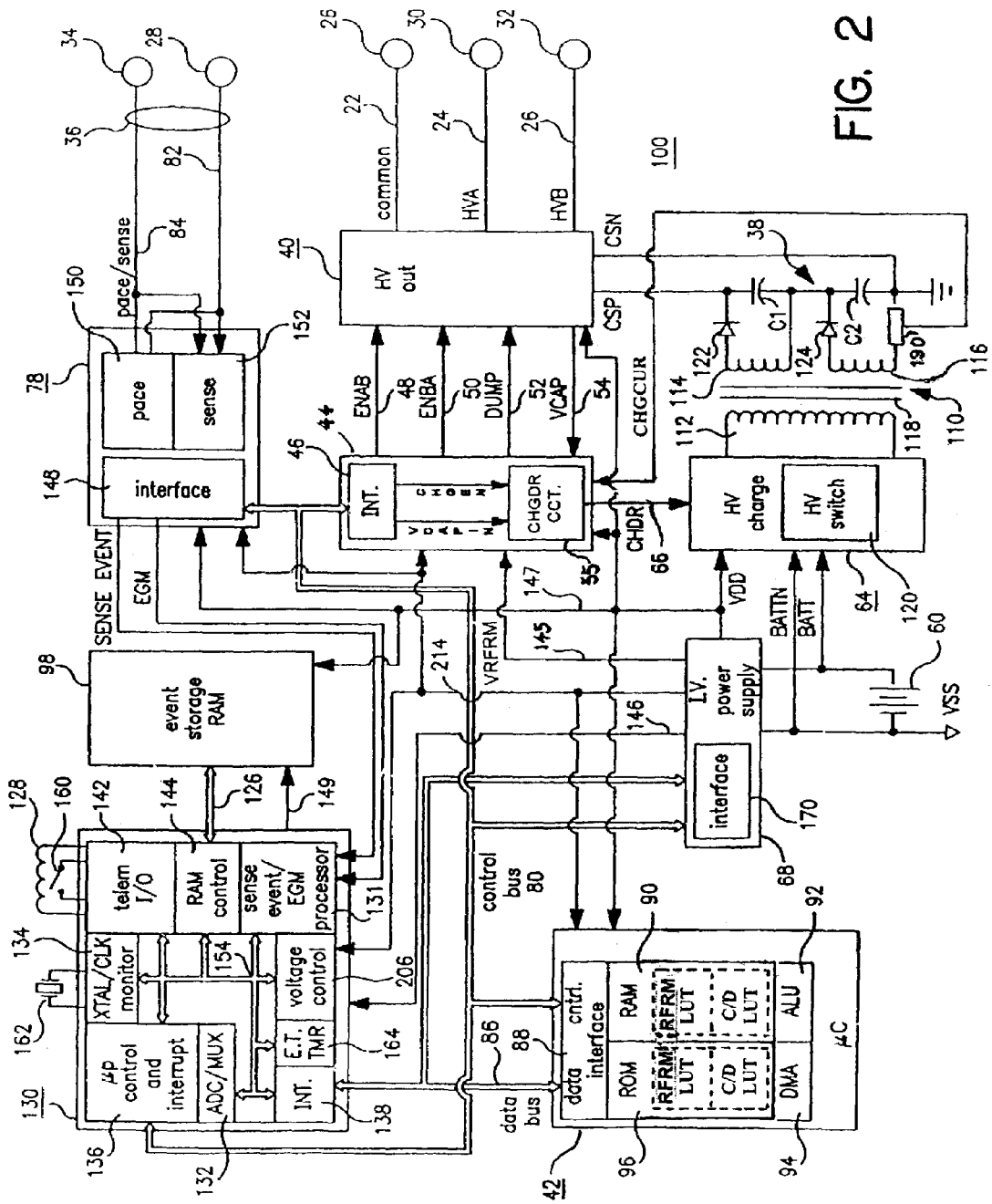
FIG. 2 is a functional block diagram illustrating an ICD system of the ICD IPG of FIG. 1 in that the present invention may be advantageously practiced.

In FIG. 1, an ICD IPG 10 and associated 14, 16 and 18 are illustrated in relation to a patient's heart 12 as in FIG. 1 of commonly assigned U.S. Pat. Nos. 5,265,588 and 5,470,341. Over the past 20 years, ICD IPGs have evolved, as described in some detail in, from relatively bulky, crude, and short-lived IPGs simply providing high energy defibrillation shocks to complex, long-lived, and miniaturized IPGs providing a wide variety of pacing, cardioversion and defibrillation therapies. Numerous other programmable functions have been incorporated including enhanced capacity to detect and discriminate cardiac arrhythmias, data storage and uplink telemetry of data related to arrhythmia episodes and applied therapies, provision of staged therapies appropriate to the detected arrhythmia, for example. At the same time, numerous improvements have been made in C/D leads and electrodes that have enabled the C/D energy to be precisely delivered about selected upper and lower heart chambers and thereby dramatically reducing the delivered shock energy required to cardiovert or defibrillate the heart chamber. The IPG 10 comprises the hermetically sealed, metallic housing 22 and a multi-lumen connector header 24 that contains separate connector blocks and ports for receiving and electrically and mechanically attaching the proximal connector ends of the leads 14, 16 and 18. The feedthroughs (not shown) extend from the connector blocks (not shown) within the connector header 24 and the internal high voltage and low voltage circuit within the housing 22 in a manner well known in the art.

The C/D leads 14, 16 and 18 bear relatively large surface area C/D electrodes 30, 32 and 26, respectively that are located in, on or about the heart 12. C/D lead 14 extends subcutaneously and terminates distally in a subcutaneous electrode 30, which is intended to be mounted subcutaneously in the region of the left chest. C/D lead 16 extends transvenously and terminates distally in an elongated coil CS electrode 32 that is located in the coronary sinus and great vein region of the heart 12 and extends around the heart from a point within the opening of the coronary sinus to a point in the vicinity of the left atrial appendage. Ventricular C/D lead 18 extends transvenously and is provided with an elongated electrode coil 26 that is located in the right ventricular chamber of the heart 12. C/D shocks can be applied between selected C/D electrodes.

The ICD IPG 10 preferably further incorporates atrial and/or ventricular EGM sensing capabilities for detecting atrial and/or ventricular arrhythmias. Ventricular lead 18 also includes a ventricular pace/sense electrode 34 that takes the form of a helical coil that is screwed into the myocardial tissue of the right ventricle. Lead 18 may also include an additional pace/sense electrode 28 for near field ventricular EGM sensing or a surface electrode on the IPG 10 may be paired with the helical coil electrode 34 for far field ventricular EGM sensing. Additional near field and/or far field atrial EGM sensing and atrial pacing capabilities can be provided using atrial pace/sense electrode pairs on the atrial lead 16 and/or the IPG 10.

In the illustrated system, ventricular cardiac pacing pulses are delivered between helical pace/sense electrode 34 and ring electrode 28. Pace/sense electrodes 28 and 34 are also employed to sense EGM signals characteristic of ventricular contractions. As illustrated, it is anticipated that the right ventricular C/D electrode 26 will serve as the common electrode during sequential and simultaneous pulse multiple electrode defibrillation regimens. For example, during a simultaneous pulse defibrillation regimen, shocks would simultaneously be delivered between C/D electrodes 26 and 30 and between C/D electrodes 26 and 32. During sequential pulse defibrillation, it is envisioned that shocks would be delivered sequentially between C/D electrodes 30 and 26 and between coronary sinus C/D electrode 32 and right ventricular C/D electrode 26. Single pulse, two electrode defibrillation pulse regimens may be also provided, typically between right ventricular C/D electrode 26 and coronary sinus C/D electrode 32. Alternatively, single pulses may be delivered between C/D electrodes 28 and 30. The particular interconnection of the C/D electrodes to the ICD IPG 10 will depend somewhat on that specific C/D pulse regimen is employed.

The ICD IPG 10 preferably comprises an ICD operating system that provides the operating modes and functions of the MEDTRONIC® GEM 7227 single chamber or GEM DR 7271 dual chamber ICD, IPGs that are programmable in operating mode and parameter values and interrogatable employing the MEDTRONIC® Model 9790C external programmer, for example. FIG. 2 is a functional block diagram illustrating such a single chamber ICD operating system 100 that is merely exemplary of a variety of single chamber and dual chamber ICD systems having all or some of the capabilities described above in that the capacitor reforming system and method of the present invention can be advantageously implemented. The ICD system 100 includes one or more ICs typically mounted on one or more circuit board and a PC board for mounting a number of discrete components, e.g. telemetry antenna 128, reed switch 160, crystal 162, a set of HV discrete components of the C/D sub-system, and the battery 60. If the architecture of FIG. 3 of the above-referenced '341 and '588 patents is employed, the depicted functional blocks and discrete components of FIG. 2 are arranged as part of a LV circuit board, a HV circuit board and a discrete component PC board. However, it will be understood that a single circuit board could be employed that incorporates and supports all of the system ICs. Similar ICD systems to that depicted in FIG. 2 in that the present invention can be implemented are shown, for example, in U.S. Pat. Nos. 4,830,006, 4,693,253, 4,971,058, 5,312,441, and 5,827,326, for example.

The depicted HV C/D therapy delivery sub-system comprises a DC-DC converter, powered by battery 60, which further comprises HV charging circuit 64, a discrete HV step-up transformer 110, and the HV output capacitor bank 38. The depicted HV C/D therapy delivery sub-system further comprises a HV discharge or output circuit 40 for discharging the charge on the HV output capacitor bank 38 through the C/D leads and electrodes of FIG. 1. This sub-system can be incorporated into the HV circuit board and the PC board of the above-referenced '341 and '588 patent architecture, if that architecture is followed. The charge on the HV output capacitor bank 38, comprising series connected capacitors C1 and C2 in this case, is selectively discharged through the C/D electrodes 26, 30 and 32 coupled via leads 22, 24 and 26 to the HV output circuit 40.

A typical LV circuit board incorporates one or more discrete component, IC, data and control buses, interrupt and signal lines, etc., e.g., the LV power supply 68, the pace/sense circuit 78, the event storage RAM 98, the LV control IC 130, the HV control circuit 44, the microcomputer 42, the data bus 86, and control bus 80. Not all of the signal and control lines interconnecting these blocks are shown for simplicity of illustration and because they play no role in the practice of the present invention. Most of the ICs employed in the LV circuit boards are fabricated using CMOS fabrication techniques. For example, in FIG. 2, the LV control IC 130 is preferably formed of a single CMOS IC die that performs the functions of the circuits and data and control buses depicted therein. The microcomputer 42 is depicted as formed of a further CMOS IC die, but it may be combined with the LV control IC 130 in a single CMOS IC.

The exemplary prior art ICD system 100 of FIG. 2 is powered by the battery 60 coupled to the HV charging circuit 64 and to a LV power supply 68 that provides regulated power to the LV ICs, circuit boards and certain of the discrete components of the system 100. The battery 60 preferably comprises a low voltage, high energy density, higher current output, lithium silver vanadium battery or the like that produces a voltage from about 3.2 volts when fresh to about 2.5 volts at specified end of service. The LV power supply generates a regulated supply voltage VDD that is supplied via power line 147 to a number of the illustrated circuits comprising the illustrated microcomputer 42, the pace/sense circuit 78, off-board RAM 98, the HV control and regulator circuit 44, the HV charging circuit 64 to power the DC-DC conversion switching circuit 120 and the HV output circuit 40 to power operation of certain switching circuit therein. The LV power supply 68 also includes a power-on-reset (POR) circuit that provides a POR signal on line 214 to a number of the illustrated circuits to reset logic within those circuits to a known state if a power disruption occurs in a manner well known in the art.

All of the timing and control circuits and functions depend upon the voltage and current available from the battery 60, and it is desirable to minimize current drain and voltage depletion to maximize longevity. The cardiac cycle depends on heart rate that can vary in normal sinus function between 50 and 160 bpm in a healthy human heart and can fall below or rise above that range in an unhealthy human heart. Virtually all of the ICD IPG monitoring and bradycardia pacing functions are timed from a sensed cardiac event that depends on the spontaneous heart rate or a pace event at the end of an escape interval timed out during a bradycardia episode. The microcomputer functions can be performed within a few clock cycles of a sensed event or pacing pulse, and then can revert to a low current drain, sleep mode. The continuous EGM sampling, digitizing and storage functions handled by the LV control IC 130 can be completed at 100–200 Hz EGM sampling rates. Thus, current drain is minimized in this context by minimizing the "on" time of current consuming components.

The operating modes of the ICD system 100 are controlled by the microcomputer 42, the LV CMOS IC 130, and the HV control circuit 44 following an operating program stored in ROM 96 and RAM 92 that performs all necessary computational and control functions. The microcomputer 42 comprises the typical components of a microcomputer, including the DMA controller 94 and ALU 92 and associated on-board ROM 96 and RAM 90. The program code that governs operation of the ICD system 100 is stored in ROM 96, and the operations are carried out following operating modes and parameters that are stored as operating system data in RAM 90. The operating mode and parameter data is programmable and interrogatable through downlink telemetry programming and interrogation operations that are well known in the art. Such operating modes include the enabling and disabling functions and such operating parameters include pacing pulse width and/or amplitude, sense amplifier sensitivity, event data storage, arrhythmia detection parameters, arrhythmia therapies to be delivered, etc. The ALU 92 performs the logical operations directed by the program code in response to the interrupts and control signals provided by the µP control and interrupt block 136 of LV control IC 130. Data related to the ICD itself, the patient history and the like can also be stored in the RAM 90 for interrogation and telemetry out by the telemetry I/O circuit 142 of LV control IC 130. The DMA 94 provides for direct memory access to register locations in RAM 90, event RAM 98 and ROM 96 without the need for microcomputer control in a manner well known in the art.

A bi-directional control bus 80 and certain discrete interrupt and control lines (not shown) link the input/output interface 88 of microcomputer 42 with input/output interfaces 46, 148, and 170 of HV control circuit 44, pace/sense circuit 78, and LV power supply, respectively, and with the microprocessor control and interrupt 136. These on-chip interfaces contain chip-select, address decoding and data bus logic as is typically employed with microprocessor peripherals. The bi-directional data bus 86 and internal bi-directional data and control bus 154 within LV control IC 130 and data bus 126 between event storage RAM allows the microcomputer 42 to control the movement of data between the microcomputer ROM 96 and RAM 90 and registers in event storage RAM 98.

The LV control IC 130 is required to provide inputs to and carry out many of the operations of the microcomputer 42. The LV control IC 130 provides system clock and timing, interrupt, uplink and downlink telemetry functions, ADC/MUX signal processing, sensed event EGM signal processing for arrhythmia detection and discrimination, event data storage and real-time uplink of the patient's EGM. The system clock is provided by the crystal 162 and crystal oscillator and monitoring circuit 134.

The telemetry I/O circuit receives and decodes downlink telemetry transmitted interrogation and programming commands and provides the decoded commands to the microcomputer via the data and control bus 154, µP control and interrupt circuit 136 and control bus 80. The telemetry I/O circuit 142 is also triggered by commands from the microcomputer 42 delivered via the reverse path to uplink telemetry transmit stored device, implant, and patient data from the RAM 90 or stored episode EGM data retrieved by RAM control circuit 144 from the event storage RAM 98. The telemetry I/O circuit 142 can also be commanded to uplink telemetry transmit the real time EGM signal processed by EGM sense event/waveform analysis circuit 140 and ADC/MUX 132 provided via internal data and control bus 154. Other system data, including battery voltage, HV capacitor charging time, lead impedance and pace and sensed event markers can also be uplink telemetry transmitted via I/O telemetry circuit 142. Such telemetry systems and functions are well known in the art as exemplified by commonly assigned U.S. Pat. No. 5,127,404.

Pace/sense circuit 78 of the type described in the above-referenced '341 and '588 patents, for example, includes a pacing pulse generator 150 for generating ventricular pacing pulses, an R-wave sense amplifier 152 for generating sensed event and EGM signals, and an interface 148 and other blanking and high voltage protection circuits. As noted above, dual chamber or single chamber atrial pacing and sensing functions can also or alternatively be provided employing suitable pace/sense circuit 78 and suitable far field (unipolar) or near field (bipolar) atrial electrode pairs. In the illustrated embodiment, pace/sense circuit 78 is coupled to ventricular pace/sense electrodes 28 and 34, illustrated in FIG. 1, by means of a conductors 82 and 84 in ventricular lead 36, allowing for bipolar sensing of R-waves and for delivery of bipolar pacing pulses to the ventricle of the heart 12. High voltage protection circuit is also included in pace/sense circuit 78 across the conductors 82 and 84 to protect the pacing pulse generator 150 and the sense amplifier 152 from C/D shock energy that is picked up on the pace/sense electrodes. The expiration of a pacing escape interval that is timed out in escape interval timer 164 signifies a bradycardia condition, and a pace trigger signal is generated and delivered via control bus 80 to trigger generation of a cardiac pacing pulses by the pacing pulse generator 150. The escape interval is set by the microcomputer 42 based upon a programmed in pacing rate stored in RAM 90 or a physiologic pacing rate in the case where rate responsive pacing capability is provided. A rate responsive pacing function can also be provided in the manner provided in the MEDTRONIC® GEM 7227 single chamber or GEM DR 7271 dual chamber ICD IPGs.

Moreover, bursts of high rate pacing pulses for treatment of a tachycardia detected by the arrhythmia detection algorithm can also be timed out in the escape interval timer 140 and triggered by pace trigger signals delivered via control bus 80. Sense amplifier blanking intervals following paced and sensed events are specified by microcomputer 42 via control bus 80 and interface 148. It will be understood that the pacing escape interval and the burst pacing intervals can also be established and timed out in the microcomputer 42 rather than in the escape interval timer 140. In that case, the sensed event signal can be conducted to the microcomputer interface 88 via the control bus 80 to reset the escape interval timing by the microcomputer 42.

The sensed event signals indicative of the occurrence of an R-wave (in this illustrated embodiment) are generated by a comparator stage of the sense amplifier 152 that functions by comparing the amplitude of the EGM signal to a sensitivity threshold programmed into RAM 90 by the physician in a manner well known in the art and delivered by microcomputer 42 by means of the data bus 80 and interface 148. The sensed event signals are supplied to the EGM sense event/waveform analysis circuit 140 that outputs a reset signal to the escape interval timer 164 and to the µP control and interrupt circuit 136 via data and control bus 154. The µP control and interrupt circuit 136 via data and control bus 154 responds to the sensed event signals by awakening microcomputer 42 to perform any necessary mathematical calculations, to perform tachycardia and fibrillation detection procedures, and to generate the blanking and refractory intervals Moreover, the EGM itself is directed from an amplification stage of the sense amplifier 152 to the EGM sense event/waveform analysis circuit 140. The delivered EGM is sampled and digitized in ADC/MUX 132 and delivered to the RAM control circuit 144 on a continuous basis via internal data and control bus 154. The RAM control circuit cycles EGM data through addressed registers of event storage RAM 98 on a FIFO basis to store a 20 second or so segment of EGM data until tachyarrhythmia detection criteria are satisfied, whereupon the pre-detect data is transferred to permanent storage. The RAM control circuit then stores a post-detect segment of EGM data along with the pre-detect data and an identification of the delivered therapy and response to the delivered therapy for later interrogation and telemetry out in a manner well known in the art.

The tachyarrhythmia detection criteria are specified in ROM 96 and RAM 92 and typically involves elevation of the spontaneous heart rate coupled with other onset, rate acceleration, and stability criteria and various other criteria as described, for example, in the above-referenced '006, '058, and '441 patents, for example. The spontaneous heart rate is calculated in a heart rate timer maintained by the microcomputer 42, and other characteristics of the EGM are examined to determine whether or not a high rate EGM constitutes a normal sinus rhythm or a malignant tachyarrhythmia. Spontaneous heart rate and EGM width criterion are employed in the MEDTRONIC® GEM 7227 single chamber ICD IPG, and both the atrial and ventricular heart rates and EGMs are examined with information about conduction patterns, regularity and AV dissociation in the detection and classification algorithm employed in GEM DR 7271 dual chamber ICD IPGs.

Figure 3:
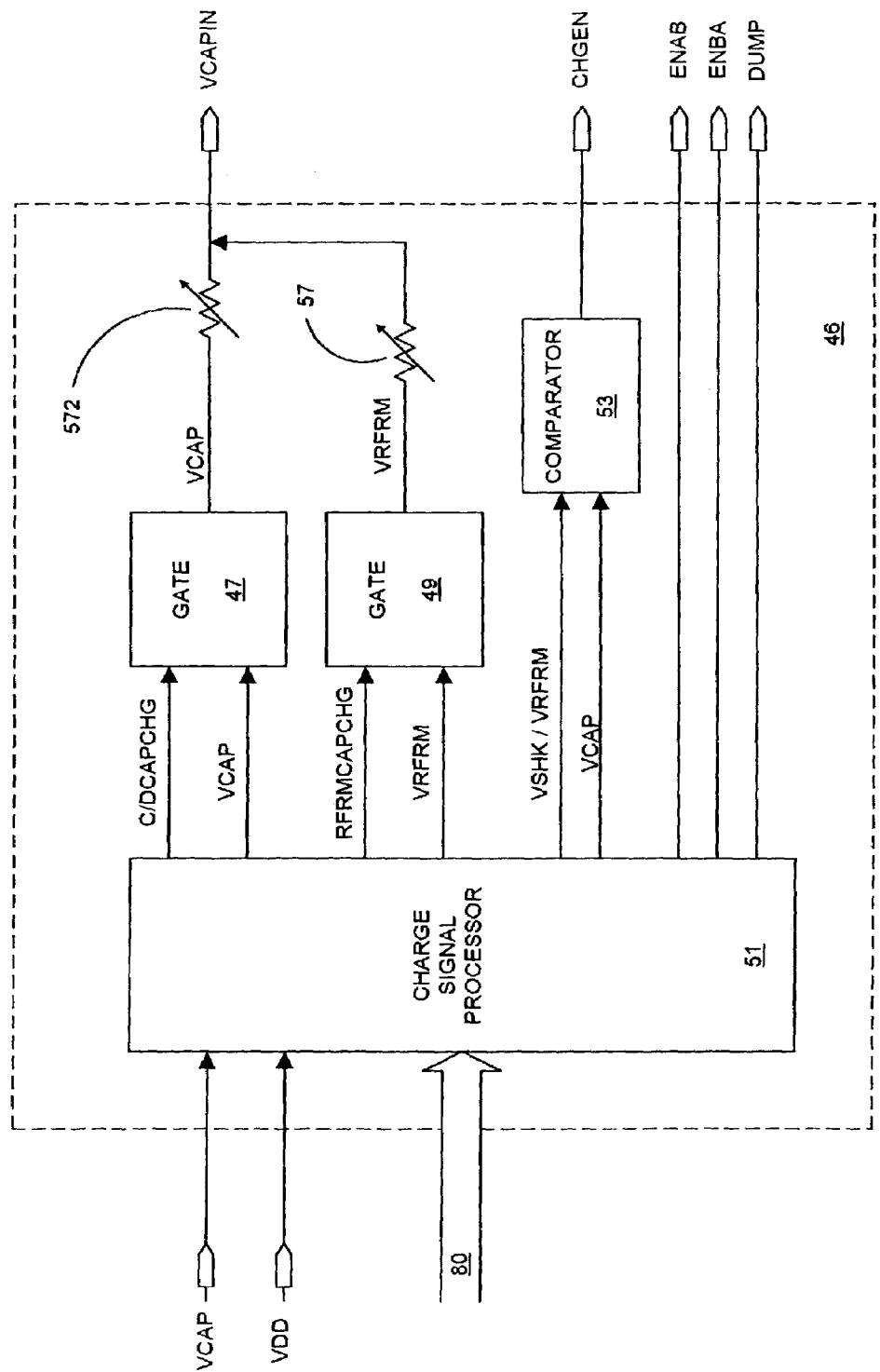
FIG. 3 is a detailed block diagram of one embodiment of circuit for setting a VCO duty cycle for charging HV output capacitors to a C/D shock energy or to a capacitor oxide layer reforming voltage in accordance with the present invention.

The functions and detailed circuit schematics of the circuit of FIG. 2 are set forth in the above-referenced '341 and '588 patents. FIGS. 3 and 4a–4b of the '588 patent specifically illustrate the HV circuit comprising the HV charging circuit 64, the HV output circuit 40 and the HV step-up transformer 110 and capacitor bank 38. With respect to the charging of the HV output capacitor bank 38, the primary coil winding 112 is coupled at one terminal to the power supply BATT input terminal through a fuse link and at its other terminal to the BATTN terminal through a duty cycle switching circuit block 120 described specifically in the above-referenced '588 patent.

When a tachyarrhythmia episode is detected and classified, the appropriate programmed burst-pacing therapy or synchronous cardioversion shock therapy or HV defibrillation therapy is delivered. The burst pacing therapy is delivered via pace/sense circuit 78, and the cardioversion and defibrillation therapies are delivered as follows. In this illustrated embodiment, the HV output circuit 40 is coupled to the output capacitor bank 38, including HV output capacitors C1 and C2, and is programmable for delivering biphasic C/D shocks to selected C/D electrodes. The HV output capacitors C1 and C2 are coupled to secondary windings 114 and 116 of HV step-up transformer 110 by means of the diodes 122 and 124. The primary winding 112 of HV step-up transformer 110 is coupled to the HV charging circuit 64.

The control circuit 44 provides three signals of primary importance to the HV output circuit 40, namely the first control signal ENAB on line 48, the second control signal ENBA on line 50, and the DUMP signal on line 52, which initiates discharge of the charge stored across the output capacitors C1 and C2. The C/D electrodes 26, 30 and 32 illustrated in FIG. 1 are shown coupled to the output circuit 40 by means of C/D leads 22, 24 and 26. For ease of understanding, these C/D leads are also labeled as "COMMON", "HVA" and "HVB". During a logic signal on ENAB, line 48, a C/D shock is delivered between electrode 30 and electrode 28. During a logic signal on ENBA, line 50, a C/D shock is delivered between C/D electrodes 32 and 26. However, other configurations are also possible. For example, subcutaneous C/D electrode 30 may be coupled to HVB conductor 26, to allow for a single pulse regimen to be delivered between electrodes 26 and 30. Moreover, the external surface of IPG housing 26 may be exposed and coupled as a remote subcutaneous C/D electrode replacing or augmenting the subcutaneous C/D electrode 30 and lead 24.

When a malignant tachyarrhythmia is detected, the LV control circuit 130 develops a C/DCAPCHG command specifying the C/D shock energy and waveform to be delivered. The C/DCAPCHG command is delivered through the control bus 80 to the interface 46 of the HV control circuit 44. In accordance with the present invention, the HV output capacitors C1 and C2 are periodically charged up in a capacitor reform charge cycle to a capacitor reform voltage and discharged through an internal resistive load described in the above-referenced '588 patent or allowed to dissipate over time in order to reform the capacitor anode and cathode oxide layers.

The VCAP signal is employed in the HV control circuit 44 to control the charging of the HV output capacitors C1 and C2 to a C/D shock therapy voltage or to a capacitor reform voltage. In the former case, the VCAP signal is employed to both control the rate of charge of the HV output capacitors C1 and C2 and to determine that the voltage on the output capacitors C1 and C2 has reached the programmed therapy voltage to initiate the delivery of the C/D shocks through discharge of the capacitors C1, C2 for a predetermined shock interval. In the latter case, the VCAP signal does not affect the rate of charge of the HV output capacitors C1 and C2 but is used to determine that the voltage on the output capacitors C1, C2 has reached the programmed capacitor reform voltage to halt charging. The VCAP signal on line 54 is proportional to the actual charge voltage on the HV output capacitors C1 and C2. For example, VCAP can vary between 0 and 1.2 volts as the actual charge voltage varies between 0 and 840 volts, respectively.

The HV output capacitors C1 and C2 are charged as quickly and as efficiently as possible in order to deliver the biphasic C/D shock to the selected C/D electrodes as soon as possible. The shock interval or width may be a programmed shock width or may be a function of the magnitude of the VCAP signal as the capacitors are discharged. In other words, the discharge may be for a predetermined time interval or until the voltages have discharged to a desired voltage. The C/D shock energy delivered to the heart is directly controlled by controlling the charge and discharge voltage represented by the VCAP signal.

The VCAP signal is employed to charge the HV output capacitors C1 and C2 to the programmed voltage to deliver a C/D shock as quickly as possible by controlling the duty cycle of a charge drive (CHGDR) signal on line 66 that is supplied by HV control circuit 44 to charge the HV output capacitors C1 and C2. The HV output capacitors C1 and C2 are charged by oscillations of the high frequency, HV transformer 110 operating in a well-known "flyback" fashion in the manner disclosed in detail in the above-referenced '341 and '588 patents. The transformer primary winding 112 is alternately coupled between the positive battery terminal and ground for an "on" time to build a magnetic field and then open-circuited for an "off" time to allow the field in the primary winding 112 to collapse. A high voltage is induced in the secondary windings 114 and 116 by the collapse, to charge the HV output capacitors C1 and C2 through diodes 122 and 124. The CSP and CSN voltage across the capacitor bank 38 is monitored in the HV output circuit 40, and a VCAP voltage is developed that is proportional to the actual output capacitor voltage and applied on line 54 to the HV control circuit 44. The HV control circuit 44 determines when the VCAP voltage indicates that the HV output capacitors are fully charged to a programmed voltage and terminates the CHGDR signal.

As shown in FIG. 4a of the above-referenced '588 patent, the switching circuit 120 includes a power FET in series with the transformer primary winding 112 having a first zener diode coupled across its source and drain terminals and a second zener diode coupled across its gate and drain. The CHGDR signal is applied to the power FET gate, and the power FET gate is rendered conductive or switched "on" during the CHGDR "on" time and rendered non-conductive or switched "off" during the CHGDR "off" time. When the power FET is rendered conductive by the CHGDR signal applied at its gate input terminal, it allows current to pass through the primary coil winding 112 of the HV step-up transformer 110. The switching of the power FET "on" and "off" effects the charging of the output capacitors C1 and C2.

The CHGDR signal "off" time is established by a VCO within the HV control circuit 44, particularly the CHGDR circuit 55 shown in FIG. 2, that responds to an input current VCAPIN developed in the interface 46 as described below. In accordance with one embodiment of the present invention shown in FIGS. 2 and 3, the VCO input voltage depends upon whether the charge cycle is triggered by a C/DCAPCHG command generated in response to detection of a malignant tachyarrhythmia or a RFRMCAPCHG command.

As noted above, the C/DCAPCHG command and the RFRMCAPCHG command are generated in the LV control IC 130 and transmitted over control bus 80 to the interface 46 of the control circuit 44. The LV control IC 130 also transmits the programmed shock voltage (VSHK) and reform voltage (VRFRM) that the HV output capacitors are to be charged to in association with the C/DCAPCHG command and the RFRMCAPCHG command, respectively. For example, VSHK and VRFRM may be both set to 1.2 volts to represent an 840 volt charge on HV output capacitors C1 and C2. Charging of HV output capacitors C1 and C2 is terminated when VCAP equals 1.2 volts, which is proportional to the 840 volt charge as noted above. Furthermore, the LV control IC 130 transmits commands in association with the C/DCAPCHG command that establish the C/D shock therapy waveform using discharge paths ENBA and ENAB and that initiate the discharge of the HV output capacitors C1 and C2 after they are charged up and the continued detection of the tachyarrhythmia is confirmed.

A DUMP command can also be generated by LV control IC 130 and transmitted over control bus 80 to the interface 46 of the control circuit 44 to discharge the HV output capacitors through an internal load as described in the above-referenced '588 patent. The DUMP command initiates the discharge portion of the reform charge and discharge cycle or aborts delivery of the C/D shock if the continued detection of the tachyarrhythmia is not confirmed following charging of the HV output capacitors C1 and C2. However, it should be noted that the DUMP command can be eliminated in practice so that the charge on the HV output capacitors C1 and C2 simply slowly dissipates over time.

When the therapy delivery charge cycle is initiated by a C/DCAPCHG command, the "on" time of the CHGDR signal is a constant time or pulse width, but the "off" time of the CHGDR signal is inversely proportional to the VCAP signal as shown in FIG. 9 of the above-referenced '588 patent. In one example disclosed in the above-referenced '588 patent, the "on" time is 11 microseconds but is shortened to 4 microseconds if the battery voltage falls to a voltage VREF. The "off" time comprises a fixed time of 3 microseconds and a variable time ranging between 235 microseconds when VCAP equals zero volts and 1 microsecond when VCAP equals 1000 volts. In this way, a C/D CHGDR signal is developed wherein the "off" time decreases as VCAP increases, and the charging time of the HV output capacitors C1 and C2 to the programmed C/D shock voltage is reduced. The decreased "off" time is limited by the necessity of avoiding saturation of the transformer 110.

The charging time of the HV output capacitors C1 and C2 to the programmed C/D shock voltage depends upon a number of factors including the designed beginning of life (BOL) charge time, the state of the capacitor oxide layers, the impedance of the charging circuit presented to the battery, and the condition of the battery. For example, the designed (BOL) charge time may be 6–30 seconds depending upon ICD model, and that charge time may double as the battery depletes through use to an end of life (EOL) voltage.

In accordance with the present invention, the VCAP signal is not employed in this manner to modulate the duty cycle of the CHGDR signal in a capacitor reform charge cycle initiated by a RFRMCAPCHG command. Instead, the "on" time and the "off" time of the CHGDR signal are preferably fixed so that the charging of the HV output capacitors C1 and C2 to the capacitor reforming voltage is at a slow rate. In one approach, the "off" time is set to be substantially longer than the "on" time. In this particular embodiment, the "on" time remains at the prevailing 11 microseconds or 4 microseconds, and the "off" time is set close to the maximum 235 microseconds. It will be understood that the prevailing "on" time could also or alternatively be shortened to decrease the rate of charging.

Referring to FIGS. 2 and 3, the capacitor reform charge cycle is initiated by a RFRMCAPCHG command generated by the LV control IC 130, delivered over the control bus 80, and received by the interface 46. The RFRMCAPCHG command is generated in response to either of a downlink telemetry transmitted capacitor reform command received from an external programmer or automatically upon expiration of a reform time period since the most recent capacitor reform charge cycle or delivery of a C/D shock. The capacitor reform time since the most recent capacitor reform charge cycle or delivery of a C/D shock can be a programmed time or a fixed time.

The interface 46, shown in greater detail in FIG. 3, generates a VCAPIN signal and a CHGEN signal that are applied to a CHGDR circuit 55. The CHGDR circuit 55 can comprise the circuitry of FIGS. 5 through 8C of the above-referenced '588 patent employing the CHGDR and VCAPIN signals as described therein. The interface circuit 46 also processes the commands received on bus 80 and the VCAP signal to develop the CHGEN signal that enables HV output capacitor charging until the VCAP signal signifies that the HV output capacitors C1 and C2 are charged to the output voltage proportional to that of VSHK or VRFRM.

In this embodiment of the present invention, the VCAPIN signal is a fixed current when the CHGEN signal is generated in response to the RFRMCAPCHG command that slows the rate of charge and increases the capacitor charge time. The VCAPIN signal is a variable current when the CHGEN signal is generated in response to the C/DCAPCHG command as described above and in the above-referenced '588 patent.

In FIG. 3, the charge signal processor 51 recognizes the input signals received on bus 80 and supplies the C/DCAPCHG command to gate 47 and the RFRMCAPCHG command to gate 49. The charge signal processor 51 also recognizes the charge voltage VSHK and VRFRM commands received on bus 80 in association with the C/DCAPCHG and RFRMCAPCHG commands, respectively.

The charge voltage VSHK or VRFRM maintained in charge signal processor 51 is compared to the VCAP voltage in comparator 53. The CHGEN signal is developed by comparator 53 as long as the VCAP voltage is less than the charge voltage VSHK or VRFRM maintained in charge signal processor 51. The CHGEN signal is applied to the CHGDR circuit 55 to enable production of the CHGDR signal as described above and in the above-referenced '588 patent.

The varying voltage VCAP is applied through the resistor 572 (corresponding to resistor 572 in FIG. 6 of the above-referenced '588 patent) to provide a varying VCAPIN current to the CHGDR circuit 55 when the C/DCAPCHG command is received on bus 80. The fixed voltage VRFRM is applied through the resistor 57 to provide a fixed VCAPIN current to the CHGDR circuit 55 when the RFRMCAPCHG command is received on bus 80. As described above, the value of the VCAPIN current determines the "off" time of the CHGDR signal on line 66 supplied to the HV charge circuit 64 and the charging time of the HV output capacitors C1 and C2.

Thus, the charge time during the capacitor reforming cycle can be slowed by the appropriate selection of the VRFRM voltage and the resistance 57. In the above-described example, a very low voltage of VCAPIN can be applied that causes the "off" time to be maintained close to the 235 microseconds maximum. The resulting capacitor reform cycle charge time can preferably be 2 to 20 times the C/D shock therapy delivery charge time.

Thus, one way of increasing the charge time and lowering the rate of charging the HV output capacitors during reforming of the oxide layers of the HV output capacitors is disclosed above. It will be understood that other ways of increasing the charge time and lowering the rate of charging the HV output capacitors appropriate to the above-described ICD architecture or to other ICD architectures will be readily apparent to those of skill in the art.

For example, more recent ICD operating systems modulate the "on" time as a function of supply voltage BATT and modulates the "off" time as a function of the charging current CHGCUR induced in the output winding 116 measured across a low resistance 190 for charging the HV capacitor C2 rather than the VCAP signal. In one example, the "on" time and the "off" time are initially nominally set to 3.2 microseconds. However, the "on" time is not allowed to restart after the time-out of the nominal 3.2 microsecond "off" time until the induced current measured between the output winding 116 and ground falls to a value near zero. Therefore, the "off" time can vary as a function of the secondary winding current to avoid saturation of the HV transformer 110. The "on" time is varied from 3.2 microseconds to about 16.0 microseconds as a function of supply voltage BATT. The supply voltage BATT is measured about every 8–16 milliseconds via interface 170, and the measured BATT value is compared to a C/D therapy look-up table C/D LUT of "on" times correlated to BATT values stored in RAM 90 (backed up in ROM 96). The "on" time determined from the look-up table is then employed until the next measurement takes place. In this way, the HV output capacitor charging time is minimized while the battery 60 is not unduly loaded and saturation of the HV transformer 110 is avoided.

In accordance with the present invention, the "on" times and/or "off" times employed to reform the oxide layers of the anode and cathode plates of the HV output capacitors C1 and C2 can be selectively decreased and/or increased, respectively, to values that optimize the results sought to be achieved in reforming the oxide layers. It is simply a matter of empirically determining the optimal "on" times and "off" times and storing them in a separate reform look-up table (RFRM LUT in FIG. 2) correlated to the measured BATT values in RAM 90, backed up in ROM 96. In this case, the "off" times may be prolonged such that the induced current in the secondary winding 116 falls to zero well before the "off" time times out. In addition, it may be only necessary to measure supply voltage BATT at the outset of the reform charge to determine an appropriate set of "on" times and "off" times employed throughout the reform charge cycle. The RFRM LUT "on" times may be shortened in relation to the C/D therapy "on" times and/or the RFRM LUT "off" times may be lengthened in relation to the C/D therapy "off" times.

This approach is advantageous because as new model ICDs are developed, they employ differing batteries 60, HV charge circuits 64, HV transformers 110, and HV output capacitors C1 and C2. The C/D LUT of "on" times correlated to BATT values and the RFRM LUT of "on" times and "off" times correlated to BATT values can be readily derived for the particular characteristics of these components from battery BOL to EOL and stored in ROM 96 and RAM 90.

In a further variation, the same reform look-up table values of "on" and "off" times can be employed to maintain the voltage on the HV output capacitors C1 and C2 during the time following a C/D therapy charge cycle and discharge of the voltage as a C/D therapy shock as described in the above-referenced co-pending ('P-9171) application.

Thus, the above described approaches provide methods and apparatus that establish a C/D therapy charge "on" time and a C/D therapy charge "off" time that determines the C/D therapy charge rate, and a reform charge "on" time and a reform charge "off" time that determines the reform charge rate, wherein the reform charge "off" time is longer than the C/D therapy charge "off" time. The reform charge "off" time can be made longer than the C/D therapy charge "off" time over the entire reform charge or at least a portion of the reform charge, and/or the reform charge "on" time can be made shorter than the C/D therapy charge "on" time over the entire reform charge or at least a portion of the reform charge.

Figure 4:
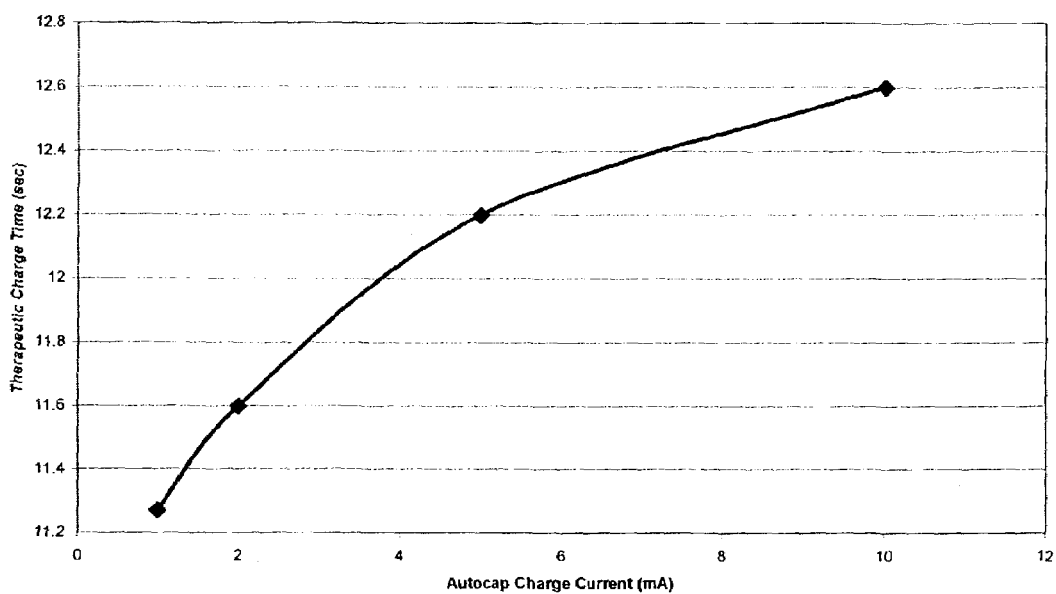
FIG. 4 is a graphical depiction of the time required to charge an HV output capacitor at the therapeutic charge rate after open circuit storage as a function of the reform charge rate.
Figure 5:
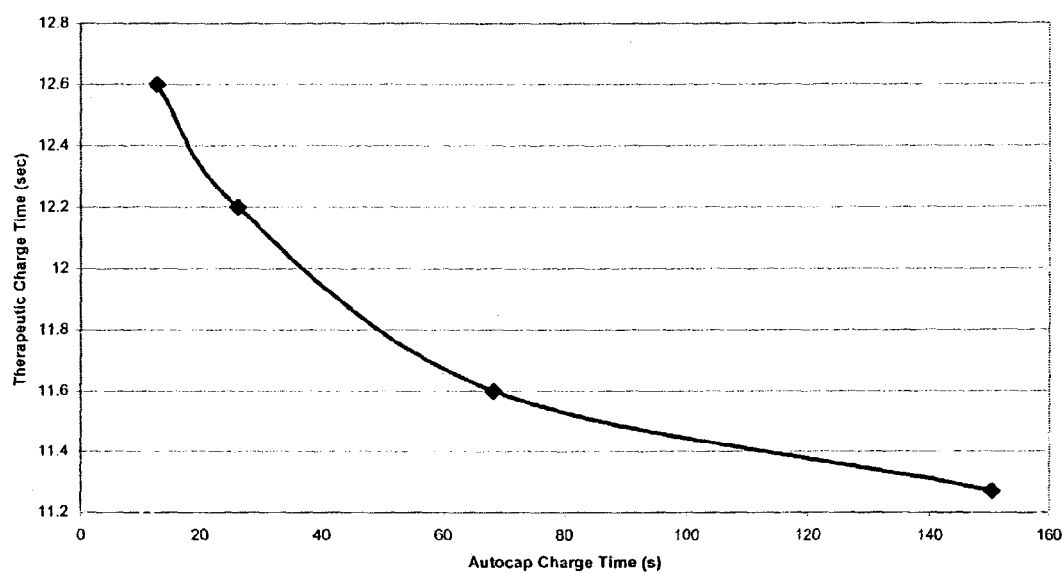
FIG. 5 is a graphical depiction of time required to charge an HV capacitor at the therapeutic charge rate after open circuit storage as a function of the reform charge time.

FIGS. 4 and 5 illustrate the benefits to be achieved by reforming HV output capacitor plate oxide layers at a slow charging current or low charging rate resulting in a prolonged reform charge time for a particular HV output capacitor design. The tested capacitor design is of the type described in commonly assigned U.S. Pat. No. 6,032,075, for example. Such flat capacitors have a hermetically sealed housing enclosing a stack of interspersed aluminum anodes and cathodes, wherein each anode and cathode is in turn formed of a stack of etched aluminum sheets upon which the oxide layers are formed. The anodes and cathodes are separated from contacting one another by paper separators, all anodes are electrically coupled together to an anode feedthrough pin, and all cathodes are electrically coupled together to a cathode feedthrough pin or the housing. The capacitor housing is filled with an electrolyte permeating the etched surfaces and the paper separator. The test results for this particular HV capacitor design can be expected to be representative of the results of the same tests performed on other In reference to FIGS. 4 and 5, the Therapeutic Charge Time is the amount of time required to charge a HV output capacitor using a 10 mA current after the capacitor has been subjected to eleven cycles of open circuit storage for 7 days at 60° C. At the completion of each 7-day cycle, the capacitor was charged at 37° C. using the indicated reformation charge current/time. Four different reformation charge currents/times were used. Each data point represents the average value obtained from eight capacitors. A constant 10 mA charge current was used because it approximates the charge time that would be required to charge the HV capacitor to deliver a therapy near the end of the device life. Storage of the capacitor at open circuit for 7 days at 60° C. produces oxide degradation similar to that which occurs after 90 days of storage at 37° C.

The above-described techniques of slowing the reform charge time during a reform charge can be used at any time that the reform cycle is initiated either by intervention of a health care provider or automatically. The initiation can be prompted by a programmed-in command that is downlink telemetry transmitted from a programmer or other external medical device or communication system. Or the reform charge cycle can be automatically initiated upon time-out of an elapsed time from the preceding reform cycle or C/D shock delivery or upon automatic determination that the oxide layers of the HV output capacitors are degraded and need reforming. Therefore, the above-described techniques of the present invention for prolonging the reform charge time during a reform charge can be used in conjunction with any of the other above-described techniques that initiate the reform charge.

The particular embodiments disclosed above are illustrative only, as the invention may be modified and practiced in different but equivalent manners apparent to those skilled in the art having the benefit of the teachings herein. For example, the present invention may be embodied in software, firmware, hardware or combination thereof.

All patents and publications referenced herein are hereby incorporated by reference in their entireties.

It will be understood that certain of the above-described structures, functions and operations of the above-described preferred embodiments are not necessary to practice the present invention and are included in the description simply for completeness of an exemplary embodiment or embodiments.

In addition, it will be understood that specifically described structures, functions and operations set forth in the above-referenced patents can be practiced in conjunction with the present invention, but they are not essential to its practice.

It is therefore to be understood, which within the scope of the appended claims, the invention may be practiced otherwise than as specifically described without actually departing from the spirit and scope of the present invention.

What is claimed is:

1. A method of operating a cardioverter/defibrillator of the type having at least one high voltage (HV) output capacitor that comprises a cathode, a valve metal anode with a formed oxide that deforms during periods of electrical inactivity and an electrolyte and that is charged from a battery through a charging circuit and is adapted to be discharged through cardioversion/defibrillation (C/D) electrodes comprising:
   in response to a detected arrthymia, charging at least one HV output capacitor at a therapeutic charging rate substantially to a preprogrammed or maximum charge and either:
      discharging at least a portion of the charge of said at least one HV output capacitor; or
      allowing at least a portion of the charge of said at least one HV output capacitor to discharge through a non-therapeutic load; and
   periodically charging the at least one HV output capacitor at a reform charging rate that is slower than the therapeutic charging rate substantially to the preprogrammed or maximum charge to thereby reform at least a portion of a deformed oxide of said HV output capacitor.

2. A method according to claim 1, wherein the charging circuit includes a HV step-up transformer and the charging step of charging and periodically charging both further comprise:
   delivering battery energy to a primary winding of the HV step-up transformer during an "on" time to induce a charging current in a secondary winding coupled with the HV output capacitor during an "off" time that incrementally charges the HV output capacitor, and further comprising:
      establishing a C/D therapy charge "on" time and a C/D therapy charge "off" time that determines the C/D therapy charge rate; and
      establishing a reform charge "on" time and a reform charge "off" time that determines the reform charge rate.

3. A method according to claim 1, wherein the charging circuit includes a HV step-up transformer and wherein the charging and the periodically charging step both further comprise:
   delivering battery energy to a primary winding of the HV step-up transformer during an "on" time to induce a charging current in a secondary winding coupled with the HV output capacitor during an "off" time that incrementally charges the HV output capacitor, and further comprising:
      establishing a C/D therapy charge "on" time and a C/D therapy charge "off" time that determines the C/D therapy charge rate; and
      establishing a reform charge "on" time and a reform charge "off" time that determines the reform charge rate, wherein the reform charge "on" time is shorter than the C/D therapy charge "on" time over the entire reform charge or at least a portion of the reform charge.

4. A method according to claim 1, wherein the charging circuit includes a HV step-up transformer and the charging and periodically charging step both further comprise:
   delivering battery energy to a primary winding of the HV step-up transformer during an "on" time to induce a charging current in a secondary winding coupled with the HV output capacitor during an "off" time that incrementally charges the HV output capacitor, and further comprising:
      establishing a C/D therapy charge "on" time and a C/D therapy charge "off" time that determines the C/D therapy charge rate; and
      establishing a reform charge "on" time and a reform charge "off" time that determines the reform charge rate, wherein the reform charge "off" time is longer than the C/D therapy charge "off" time over the entire reform charge or at least a portion of the reform charge.

5. A method according to claim 1, wherein the charging circuit includes a HV step-up transformer and the charging and the periodically charging step both further comprise:
   delivering battery energy to a primary winding of the HV step-up transformer during an "on" time to induce a charging current in a secondary winding coupled with the HV output capacitor during an "off" time that incrementally charges the HV output capacitor, and further comprising:
      establishing a C/D therapy charge "on" time and a C/D therapy charge "off" time that determines the C/D therapy charge rate; and
      establishing a reform charge "on" time and a reform charge "off" time that determines the reform charge rate, wherein the reform charge "on" time is shorter than the C/D therapy charge "on" time and the reform charge "off" time is longer than the C/D therapy charge "off" time over the entire reform charge or at least a portion of the reform charge.

6. A method according to claim 1, wherein the charging circuit includes a HV step-up transformer and the charging and periodic charging steps both further comprise:
   delivering battery energy to a primary winding of the HV step-up transformer during an "on" time to induce a charging current in a secondary winding coupled with the HV output capacitor during an "off" time that incrementally charges the HV output capacitor, and further comprising:
      establishing a C/D therapy charge "on" time as a function of battery voltage and a C/D therapy charge "off" time as a function of the charging current induced in the secondary winding that determines the C/D therapy charge rate; and
      establishing a reform charge "on" time and a reform charge "off" time that determines the reform charge rate.

7. A method according to claim 1, wherein the charging circuit includes a HV step-up transformer and the charging and the periodically charging step both further comprise:
   delivering battery energy to a primary winding of the HV step-up transformer during an "on" time to induce a charging current in a secondary winding coupled with the HV output capacitor during an "off" time that incrementally charges the HV output capacitor, and further comprising:

establishing a C/D therapy charge "on" time as a function of battery voltage and a C/D therapy charge "off" time as a function of the charging current induced in the secondary winding that determines the C/D therapy charge rate; and establishing a reform charge "on" time and a reform charge "off" time that determines the reform charge rate, wherein the reform charge "on" time is shorter than the C/D therapy charge "on" time over the entire reform charge or at least a portion of the reform charge.

8. A method according to claim 1, wherein the charging circuit includes a HV step-up transformer and the charging and periodic charging steps further comprise delivering battery energy to a primary winding of the HV step-up transformer during an "on" time to induce a charging current in a secondary winding coupled with the HV output capacitor during an "off" time that incrementally charges the HV output capacitor, and further comprising:

establishing a C/D therapy charge "on" time as a function of battery voltage and a C/D therapy charge "off" time as a function of the charging current induced in the secondary winding that determines the C/D therapy charge rate; and establishing a reform charge "on" time and a reform charge "off" time that determines the reform charge rate, wherein the reform charge "off" time is longer than the C/D therapy charge "off" time over the entire reform charge or at least a portion of the reform charge.

9. A method according to claim 1, wherein the charging circuit includes a HV step-up transformer and the charging and periodically charging step further comprise delivering battery energy to a primary winding of the HV step-up transformer during an "on" time to induce a charging current in a secondary winding coupled with the HV output capacitor during an "off" time that incrementally charges the HV output capacitor, and further comprising:

establishing a C/D therapy charge "on" time as a function of battery voltage and a C/D therapy charge "off" time as a function of the charging current induced in the secondary winding that determines the C/D therapy charge rate; and establishing a reform charge "on" time and a reform charge "off" time that determines the reform charge rate, wherein the reform charge "on" time is shorter than the C/D therapy charge "on" time and the reform charge "off" time is longer than the C/D therapy charge "off" time over the entire reform charge or at least a portion of the reform charge.

10. A method according to claim 1, wherein the charging circuit includes a HV step-up transformer and the charging steps further comprise delivering battery energy to a primary winding of the HV step-up transformer during an "on" time to induce a charging current in a secondary winding coupled with the HV output capacitor during an "off" time that incrementally charges the HV output capacitor, and further comprising:

establishing a C/D therapy charge "on" time as a function of battery voltage and a C/D therapy charge "off" time as a function of the HV output capacitor voltage that determines the C/D therapy charge rate; and establishing a reform charge "on" time and a reform charge "off" time that determines the reform charge rate.

11. A method according to claim 1, wherein the charging circuit includes a HV step-up transformer and the charging steps further comprise delivering battery energy to a primary winding of the HV step-up transformer during an "on" time to induce a charging current in a secondary winding coupled with the HV output capacitor during an "off" time that incrementally charges the HV output capacitor, and further comprising:

establishing a C/D therapy charge "on" time as a function of battery voltage and a C/D therapy charge "off" time as a function of the HV output capacitor voltage that determines the C/D therapy charge rate; and establishing a reform charge "on" time and a reform charge "off" time that determines the reform charge rate, wherein the reform charge "on" time is shorter than the C/D therapy charge "on" time over the entire reform charge or at least a portion of the reform charge.

12. A method according to claim 1, wherein the charging circuit includes a HV step-up transformer and the charging steps further comprise delivering battery energy to a primary winding of the HV step-up transformer during an "on" time to induce a charging current in a secondary winding coupled with the HV output capacitor during an "off" time that incrementally charges the HV output capacitor, and further comprising:

establishing a C/D therapy charge "on" time as a function of battery voltage and a C/D therapy charge "off" time as a function of the HV output capacitor voltage that determines the C/D therapy charge rate; and establishing a reform charge "on" time and a reform charge "off" time that determines the reform charge rate, wherein the reform charge "off" time is longer than the C/D therapy charge "off" time over the entire reform charge or at least a portion of the reform charge.

13. A method according to claim 1, wherein the charging circuit includes a HV step-up transformer and the charging steps further comprise delivering battery energy to a primary winding of the HV step-up transformer during an "on" time to induce a charging current in a secondary winding coupled with the HV output capacitor during an "off" time that incrementally charges the HV output capacitor, and further comprising:

establishing a C/D therapy charge "on" time as a function of battery voltage and a C/D therapy charge "off" time as a function of the HV output capacitor voltage that determines the C/D therapy charge rate; and establishing a reform charge "on" time and a reform charge "off" time that determines the reform charge rate, wherein the reform charge "on" time is shorter than the C/D therapy charge "on" time and the reform charge "off" time is longer than the C/D therapy charge "off" time over the entire reform charge or at least a portion of the reform charge.

14. A cardioverter/defibrillator adapted to deliver an electrical cardioversion/defibrillation (C/D) therapy through C/D electrodes in response to a malignant tachyarrhythmia of a heart comprising:

a battery;

a high voltage (HV) step-up transformer having a primary winding and at least one secondary winding at least one HV output capacitor coupled to the secondary winding, the HV output capacitor comprising a cathode, a valve metal anode having an oxide layer formed on a majority of exposed surfaces of the anode, and a working electrolyte;

charging means coupled to the battery and the primary winding and adapted to be operated to charge the HV output capacitor coupled to the secondary winding to a predetermined C/D therapy voltage;

first means for establishing a C/D therapy charge rate that determines a C/D therapy charge time;

C/D therapy delivery means for operating the charging means at the C/D therapy charge rate to charge the HV output capacitor to the predetermined C/D therapy voltage and for discharging a C/D therapy HV output capacitor through the C/D electrodes;

second means for establishing a reform charge rate slower than the C/D therapy charge rate; and capacitor reforming means for operating the charging means at the reform charge rate to charge the HV output capacitor to substantially the predetermined C/D therapy voltage to thereby reform the oxide layer.

15. A cardioverter/defibrillator according to claim 14, wherein:

the charging means further comprises means for applying battery energy to the primary winding of the HV step-up transformer during an "on" time to induce a charging current in the secondary winding coupled with the HV output capacitor during an "off" time that incrementally charges the HV output capacitor; and wherein the first means establishes a C/D therapy charge "on" time and a C/D therapy charge "off" time that determines the C/D therapy charge rate; and wherein the second means establishes a reform charge "on" time and a reform charge "off" time that determines the reform charge rate.

16. A cardioverter/defibrillator according to claim 14, wherein:

the charging means further comprises means for applying battery energy to the primary winding of the HV step-up transformer during an "on" time to induce a charging current in the secondary winding coupled with the HV output capacitor during an "off" time that incrementally charges the HV output capacitor;

the first means establishes a C/D therapy charge "on" time and a C/D therapy charge "off" time that determines the C/D therapy charge rate; and the second means establishes a reform charge "on" time and a reform charge "off" time that determines the reform charge rate, wherein the reform charge "on" time is shorter than the C/D therapy charge "on" time over the entire reform charge or at least a portion of the reform charge.

17. A cardioverter/defibrillator according to claim 14, wherein:

the charging means further comprises means for applying battery energy to the primary winding of the HV step-up transformer during an "on" time to induce a charging current in the secondary winding coupled with the HV output capacitor during an "off" time that incrementally charges the HV output capacitor;

the first means establishes a C/D therapy charge "on" time and a C/D therapy charge "off" time that determines the C/D therapy charge rate; and the second means establishes a reform charge "on" time and a reform charge "off" time that determines the reform charge rate, wherein the reform charge "off" time is longer than the C/D therapy charge "off" time over the entire reform charge or at least a portion of the reform charge.

18. A cardioverter/defibrillator according to claim 14, wherein:

the charging means further comprises means for applying battery energy to the primary winding of the HV step-up transformer during an "on" time to induce a charging current in the secondary winding coupled with the HV output capacitor during an "off" time that incrementally charges the HV output capacitor;

the first means establishes a C/D therapy charge "on" time and a C/D therapy charge "off" time that determines the C/D therapy charge rate; and the second means establishes a reform charge "on" time and a reform charge "off" time that determines the reform charge rate, wherein the reform charge "on" time is shorter than the C/D therapy charge "on" time and the reform charge "off" time is longer than the C/D therapy charge "off" time over the entire reform charge or at least a portion of the reform charge.

19. A cardioverter/defibrillator according to claim 14, wherein:

the charging means further comprises means for applying battery energy to the primary winding of the HV step-up transformer during an "on" time to induce a charging current in the secondary winding coupled with the HV output capacitor during an "off" time that incrementally charges the HV output capacitor;

the first means establishes a C/D therapy charge "on" time as a function of battery voltage and a C/D therapy charge "off" time as a function of the charging current induced in the secondary winding that determines the C/D therapy charge rate; and the second means establishes a reform charge "on" time and a reform charge "off" time that determines the reform charge rate.

20. A cardioverter/defibrillator according to claim 14, wherein:

the charging means further comprises means for applying battery energy to the primary winding of the HV step-up transformer during an "on" time to induce a charging current in the secondary winding coupled with the HV output capacitor during an "off" time that incrementally charges the HV output capacitor;

the first means establishes a C/D therapy charge "on" time as a function of battery voltage and a C/D therapy charge "off" time as a function of the charging current induced in the secondary winding that determines the C/D therapy charge rate; and the second means establishes a reform charge "on" time and a reform charge "off" time that determines the reform charge rate, wherein the reform charge "on" time is shorter than the C/D therapy charge "on" time over the entire reform charge or at least a portion of the reform charge.

21. A cardioverter/defibrillator according to claim 14, wherein:

the charging means further comprises means for applying battery energy to the primary winding of the HV step-up transformer during an "on" time to induce a charging current in the secondary winding coupled with the HV output capacitor during an "off" time that incrementally charges the HV output capacitor;

the first means establishes a C/D therapy charge "on" time as a function of battery voltage and a C/D therapy charge "off" time as a function of the charging current induced in the secondary winding that determines the C/D therapy charge rate; and the second means establishes a reform charge "on" time and a reform charge "off" time that determines the reform charge rate, wherein the reform charge "off" time is longer than the C/D therapy charge "off" time over the entire reform charge or at least a portion of the reform charge.

22. A cardioverter/defibrillator according to claim 14, wherein:

the charging means further comprises means for applying battery energy to the primary winding of the HV step-up transformer during an "on" time to induce a charging current in the secondary winding coupled with the HV output capacitor during an "off" time that incrementally charges the HV output capacitor;

the first means establishes a C/D therapy charge "on" time as a function of battery voltage and a C/D therapy charge "off" time as a function of the charging current induced in the secondary winding that determines the C/D therapy charge rate; and the second means establishes a reform charge "on" time and a reform charge "off" time that determines the reform charge rate, wherein the reform charge "on" time is shorter than the C/D therapy charge "on" time and the reform charge "off" time is longer than the C/D therapy charge "off" time over the entire reform charge or at least a portion of the reform charge.

23. A cardioverter/defibrillator according to claim 14, wherein:

the charging means further comprises means for applying battery energy to the primary winding of the HV step-up transformer during an "on" time to induce a charging current in the secondary winding coupled with the HV output capacitor during an "off" time that incrementally charges the HV output capacitor;

the first means establishes a C/D therapy charge "on" time as a function of battery voltage and a C/D therapy charge "off" time as a function of the HV output capacitor voltage that determines the C/D therapy charge rate; and the second means establishes a reform charge "on" time and a reform charge "off" time that determines the reform charge rate.

24. A cardioverter/defibrillator according to claim 14, wherein:

the charging means further comprises means for applying battery energy to the primary winding of the HV step-up transformer during an "on" time to induce a charging current in the secondary winding coupled with the HV output capacitor during an "off" time that incrementally charges the HV output capacitor;

the first means establishes a C/D therapy charge "on" time as a function of battery voltage and a C/D therapy charge "off" time as a function of the HV output capacitor voltage that determines the C/D therapy charge rate; and the second means establishes a reform charge "on" time and a reform charge "off" time that determines the reform charge rate, wherein the reform charge "on" time is shorter than the C/D therapy charge "on" time over the entire reform charge or at least a portion of the reform charge.

25. A cardioverter/defibrillator according to claim 14, wherein:

the charging means further comprises means for applying battery energy to the primary winding of the HV step-up transformer during an "on" time to induce a charging current in the secondary winding coupled with the HV output capacitor during an "off" time that incrementally charges the HV output capacitor;

the first means establishes a C/D therapy charge "on" time as a function of battery voltage and a C/D therapy charge "off" time as a function of the HV output capacitor voltage that determines the C/D therapy charge rate; and the second means establishes a reform charge "on" time and a reform charge "off" time that determines the reform charge rate, wherein the reform charge "off" time is longer than the C/D therapy charge "off" time over the entire reform charge or at least a portion of the reform charge.

26. A cardioverter/defibrillator according to claim 14, wherein:

the charging means further comprises means for applying battery energy to the primary winding of the HV step-up transformer during an "on" time to induce a charging current in the secondary winding coupled with the HV output capacitor during an "off" time that incrementally charges the HV output capacitor;

the first means establishes a C/D therapy charge "on" time as a function of battery voltage and a C/D therapy charge "off" time as a function of the HV output capacitor voltage that determines the C/D therapy charge rate; and the second means establishes a reform charge "on" time and a reform charge "off" time that determines the reform charge rate, wherein the reform charge "on" time is shorter than the C/D therapy charge "on" time and the reform charge "off" time is longer than the C/D therapy charge "off" time over the entire reform charge or at least a portion of the reform charge.

27. A cardioverter/defibrillator adapted to deliver a cardioversion/defibrillation (C/D) shock to a patient's heart through C/D electrodes in response to a malignant tachyarrhythmia of the heart comprising:

a battery;

at least one HV output capacitor comprising a cathode, a valve metal anode having a formed metal oxide dielectric, and an electrolyte;

charging means coupled to the battery and the HV output capacitor and adapted to be operated to charge the HV output capacitor to one of a C/D therapy voltage or a capacitor reform voltage to reform the metal oxide dielectric;

first means for establishing a C/D therapy charge rate that determines a C/D therapy charge time;

C/D therapy delivery means for operating the charging means at the C/D therapy charge rate to charge the HV output capacitor to the C/D therapy voltage and for discharging a C/D therapy HV output capacitor through the C/D electrodes to deliver the C/D shock to the patient's heart;

second means for establishing a reform charge rate slower than the C/D therapy charge rate; and capacitor reforming means for operating the charging means at the reform charge rate to charge the HV output capacitor to the reform voltage to reform the metal oxide dielectric.

28. A computer readable medium containing instructions for performing a method of operating a cardioverter/defibrillator of the type having at least one high voltage (HV) output capacitor that comprises a cathode, a valve metal anode with a formed oxide layer that progressively deforms during periods of electrical inactivity and an electrolyte and that is charged from a battery through a charging circuit and is adapted to be discharged through cardioversion/defibrillation (C/D) electrodes comprising:

instructions to, in response to a detected arrthymia, charge at least one HV output capacitor at a therapeutic charging rate to a preprogrammed or maximum charge and either discharging at least a portion of the charge of said at least one HV output capacitor or allowing at least a portion of the charge of said at least one HV output capacitor to discharge through a non-therapeutic load; and instructions for periodically charging the at least one HV output capacitor to the preprogrammed or maximum charge at a reform charging rate that is slower than the therapeutic charging rate to thereby reform at least a part of a deformed oxide portion of an oxide layer.

29. A computer readable medium according to claim 28, wherein said instructions for periodically charging the at least one HV output capacitor further comprise:

instructions for inhibiting said periodically charging if the instructions to, in response to a detected arrthymia, charge at least one HV output capacitor at a therapeutic charging rate to a preprogrammed or maximum charge were previously performed during a predetermined period of time.

30. A computer readable medium according to claim 29, wherein said predetermined period of time comprises at least a one of: a number of seconds, a number of minutes, a number of hours, a number of weeks, a number of months, a fraction of any of the foregoing.

31. A computer readable medium according to claim 28, wherein said reform charging rate comprises a rate approximately one-half to approximately one-twentieth the therapeutic charging rate.

32. A computer readable medium according to claim 29, wherein said predetermined period of time is either preprogrammed or stored in a computer readable memory storage structure.

33. A computer readable medium according to claim 32, wherein said computer readable memory storage structure comprises a look up table.

* * * * *